United States Patent

Bernareggi et al.

[11] 4,252,824
[45] Feb. 24, 1981

[54] AMINO-ETHANOL DERIVATIVES

[75] Inventors: Virgilio Bernareggi, Cologne Monzese; Giuseppe Crespi, Arese; Giuseppe Bugada, Bergamo, all of Italy

[73] Assignee: Valeas S.R.L., Industria Chimica e Farmaceutica, Milan, Italy

[21] Appl. No.: 740,658

[22] Filed: Nov. 10, 1976

[30] Foreign Application Priority Data

Nov. 12, 1975 [GB] United Kingdom ............... 46677/75

[51] Int. Cl.³ ...................... A01N 33/02; C07C 91/22
[52] U.S. Cl. .................... 424/330; 260/348.11; 260/501.18; 260/544 N; 260/553 A; 260/561 R; 260/570.6; 424/316; 424/324; 560/142; 564/220; 564/363; 564/365; 564/393; 564/356; 564/399; 564/358; 564/418; 564/348; 564/305; 564/51
[58] Field of Search ............ 260/570.6, 471 C, 501.17, 260/501.79, 553 A; 424/315, 300, 322, 324, 330

[56] References Cited

U.S. PATENT DOCUMENTS

| | | | |
|---|---|---|---|
| 2,393,820 | 1/1946 | Schnider | 260/570.6 |
| 3,804,899 | 4/1974 | Ebnsther et al. | 260/570.6 |
| 3,875,233 | 4/1975 | Bastian et al. | 260/570.6 X |
| 3,879,442 | 4/1975 | Schwender et al. | 260/570.6 X |
| 3,933,913 | 1/1976 | Colella et al. | 260/570.6 |
| 3,937,838 | 2/1976 | Wetterin et al. | 260/570.6 X |
| 3,943,173 | 3/1976 | Colella et al. | 260/570.6 |
| 3,950,422 | 4/1976 | Kaplan | 260/570.6 |
| 3,969,410 | 7/1976 | Mentrump et al. | 260/570.6 |
| 4,003,930 | 1/1977 | Hanck et al. | 260/570.7 |

OTHER PUBLICATIONS

Wagner et al., "Synthetic Organic Chemistry," pp. 645 and 660 (1953).

Primary Examiner—Robert V. Hines
Attorney, Agent, or Firm—Stevens, Davis, Miller & Mosher

[57] ABSTRACT

New compounds of the formula

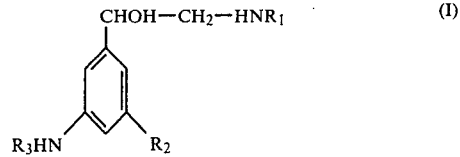

are disclosed wherein
$R_1 = B$, linear or branched alkyl-radical with from 1 to 6 carbon atoms, cycloalkyl radical with from 3 to 6 carbon atoms, alkylphenyl radical where the phenyl group may be in turn substituted with a hydroxy or methoxy group;
$R_2 = $ hydroxy, hydromethyl
$R_3 = $ H, alkyl with 1-4 carbon atoms, formyl, carboalkyl where the alkyl groups have 1-3 carbon atoms, carboamide group simple or mono- or di-substituted on the nitrogen atom with alkyl radicals containing 1-3 carbon atoms.

The new compounds are useful in the treatment of bronchial affections. They are endowed with unique properties in that they provide the desired bronchial dilation effect without any concomitant cardiac stimulation.

2 Claims, No Drawings

AMINO-ETHANOL DERIVATIVES

The present invention is concerned with a new class of amino-ethanol derivatives and more precisely with 1-(5-amino-3-substituted-phenyl)-2-amino-ethanol derivatives of the general formula

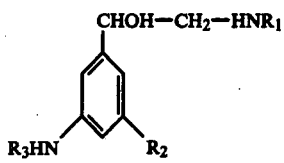

wherein:
- $R_1$=H, linear or branched alkyl-radical with from 1 to 6 carbon atoms, cycloalkyl radical with from 3 to 6 carbon atoms, alkyl-phenyl radical where the phenyl group may be in turn substituted with a hydroxy or methoxy group;
- $R_2$=hydroxy, hydroxymethyl
- $R_3$=H, alkyl with 1–4 carbon atoms, formyl, carboalkyl where the alkyl group has 1–3 carbon atoms, carboamide group simple or mono- or di-substituted on the nitrogen atom with alkyl radicals containing 1–3 carbon atoms.

The new compounds according to the present invention are endowed with a predominant $\beta_2$-receptor stimulant action, responsible for bronchospasmolysis. It is known that the search for more specific beta-2 adrenergic agents was catalyzed by the discovery of two different beta receptors. Lands AM and Brown TT Jr. Proc. Soc. Exp. Ciol Med 116:331. (1964). The beta-1 receptors increase cardiac rate and force, relax intestinal smooth muscle and stimulate lypolysis. The beta-2 receptors are concerned with relaxation of bronchial, uterine and vascular smooth muscle. It is known that catecholamine analogs and non specific $\beta_2$-adrenergic agonists, used as bronchodilators, have been prepared for some years. These compounds are characterized from the structure point of view, by an ethanol-amine chain bound to a phenyl ring bearing, respectively in the meta- and para- position with respect to the ethanolamine chain, and thus in ortho-position between them, two hydroxy or hydroxy-methyl groups. In some cases one of the two hydroxy-groups has been substituted with different groups of comparable acidity. Howver all the compounds prepared to date, although some of them are widely used clinically as bronchodilators, present the constant problem of causing a high incidence of cardiovascular side-effects due the $\beta_1$-receptor stimulation in cardiac and vascular smooth muscle. Moreover those compounds containing two ortho hydroxy-groups have a short duration of effectiveness because they are rapidly metabolized by catechol O-methyltransferase (COMT). Attempts have also been made to prepare some catecholamine analogs comprising two hydroxy-groups in the 3,5-position on the phenyl ring, with respect to the ethanol-amine chain, rather than in the usual 3,4-position. However these compounds have shown quite unsatisfactory properties thus discouraging one from preparing 3,5-substituted phenyl-ethanol amines and buttressing the commonly accepted idea that the ortho-position between them of two hydroxy-groups (or equivalent groups) on the phenyl ring of phenyl ethanol-amines is an essential element to have good bronchodilator compounds. It is thus quite unexpected what now has been found by us that the compounds of formula (I) are strong bronchodilators devoid of any activity on the cardiac muscle at the doses active on the bronchi smooth muscle. Moreover the new compounds are in no way metabolized by COMT and thus have a long-lasting activity in the organism.

The present invention also relates to the process of preparation of the new compounds of formula (I). For the sake of clarity we outline separately the process for the preparation of compounds (I) where $R_2$=CH$_2$OH (process A) and the process for the preparation of compounds (I) where $R_2$=OH (process B), by indicating hereinafter their essential steps, while the operative details will be furnished in the successive illustrative examples.

PROCESS A a—The 5-nitro isophthaloil chloride monomethyl ester, prepared starting from 5-nitroisophthalic acid according to known processes (F. Muller, Ber. 42, 433 (1909). JMC 6, 24 (1963);

D. Pitre, L. Fumagalli, E. Lorenzetti "I Farmaco" Ed. Sc. 20, 517 (1965) ) is transformed into 5-nitro-3-carbomethoxy-α-bromoacetophenone by diazomethane and HBr

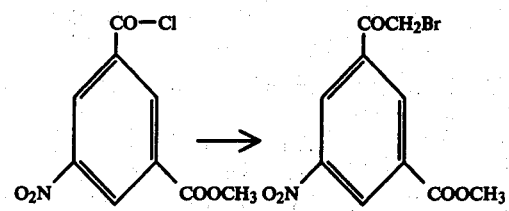

b—The substituted bromoacetophenone is reduced by NaBH$_4$ 90% to the corresponding epoxide derivative of the formula

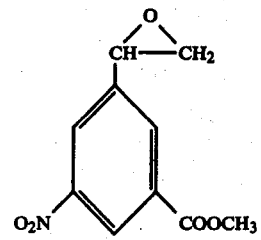

or by NaBH$_4$ 99% in suitable, inert organic solvent to the corresponding bromohydrin of the formula

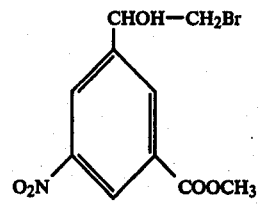

c—Both compounds obtained in step (b) may react with the desired amine to give respectively:

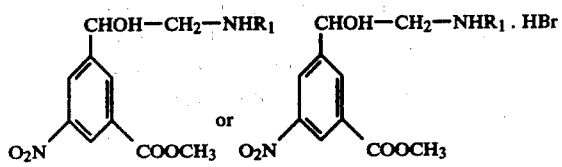

where $R_1$ has the meaning indicated for the formual (I) products.

d—The 5-nitro compound, as free base, is reduced to the corresponding 5-amino compound with hydrogen on a Pd/C catalyst

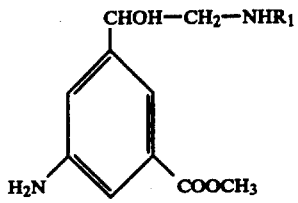

If starting from the so-prepared 1-(5-amino-3-carbomethoxy)phenyl-2-aminoethanol (II), the products of formula (I) have to be prepared where (always supposing that $R_1$ is as defined and
$R_2 = CH_2OH$)
$R_3 = H$
the group —COOCH$_3$ is reduced to —CH$_2$OH by means of LiAlH$_4$.

If the products of formula (I) have to be prepared where $R_3$ = carboalkyl the product (I) where $R_3$ = H, obtained as previously defined, is reacted, as free base, with the appropriate carboalkyl chloride or, as hydrochloride, with the appropriate anhydride.

If the products of formula (I) have to be prepared where $R_3$ = alkyl with 1–4 carbon atoms the compound (II) is firstly reacted first with the appropriate carboalkyl chloride to obtain the carboalkyl derivative of the formula

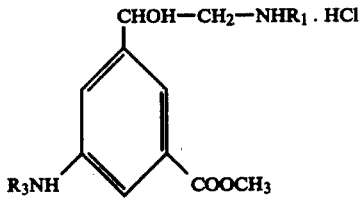

where $R_3$ = carboalkyl radical and the thus obtained compound is treated with LiAlH$_4$ obtaining the product of the formula

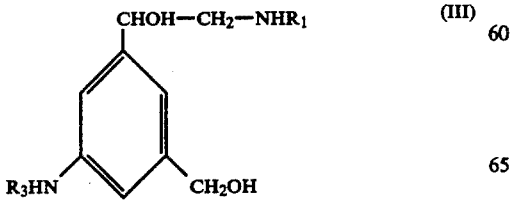

where $R_3$ = alkyl radical (III).

Obviously the above product (III) may also be obtained by treating with LiAlH$_4$ the carboalkyl derivative obtained from the product (II) as above defined.

If the products of formula (I) have to be prepared where $R_3$ = carboamide group
the compound (II) is firstly reacted with the appropriate isocyanate to obtain the ureidoderivative of the formula

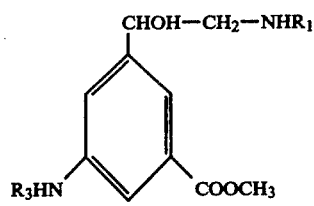

where $R_3$ = carboamido group simple or mono- or di-substituted on the nitrogen atom with alkyl radicals containing 1–3 carbon atoms and these compounds are reduced with LiAlH$_4$ to give the compounds of formula

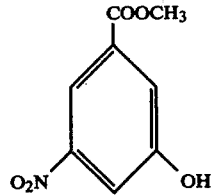

where $R_3$ is as above defined.

PROCESS B a—This process starts from the 5-nitro-3-hydroxy benzoic acid, a known compound prepared starting from 3,5-dinitrobenozoic acid according to known processes (E. Epstein, M. Meyer, J. AM. Chem. Soc. 77, 4059 (1955)), which is transformed into 5-nitro-3-hydroxymethyl benzoate of the formula

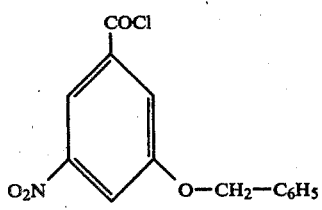

by means of methyl alcohol in the presence of a mineral acid as catalyst.

This compound is transformed into 5-nitro-3-benzyloxy benzoyl chloride of the formula by treatment with benzyl chloride and then with PCl$_5$. The benzoyl chloride is reacted with diazomethane and HBr to give the corresponding bromoacetophenone

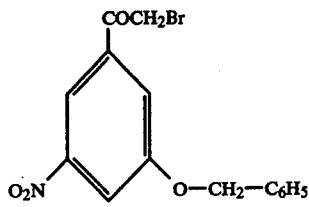

b—The bromacetophenone is reduced by NaBH$_4$ 90% to the corresponding expoxide derivative of the formula

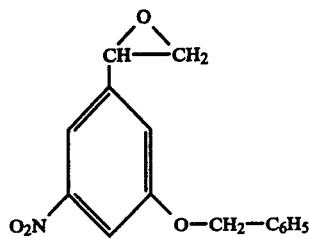

or by NaBH$_4$ 99% in suitable inert organic solvent to the corresponding bromohydrin of the formula

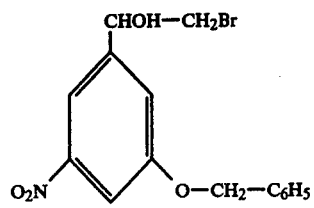

c—The above compounds dissolved in a suitable inert, organic solvent may be reacted with the desired amine to give

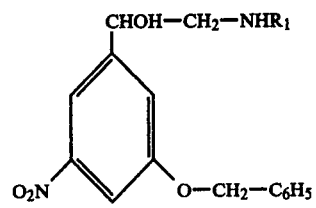

(where R$_1$ may have any meaning indicated for the formula (I)), respectively as free base (starting from the epoxy compound) or as hydrobromide (starting from the bromohydrin).

d—The 5-nitro-ethanolamine compound (as hyrochloride) is reduced to the corresponding 5-amino compond with hydrogen on a PtO$_2$ catalyst $$CHOH-CH_2-NHR_1 \cdot HCl \quad (IV)$$

(benzene ring with H$_2$N and O-CH$_2$-C$_6$H$_5$ substituents)

e—By debenzylation with hydrogen on a Pd/C catalyst the product of formula (I) is obtained where
R$_2$=OH
R$_3$=H Starting from the compound (IV) the product of formula (I) are prepared where
R$_3$=carboalky radical by reaction with the appropriate anhydride and then by debenzylation with hydrogen on a Pd/C catalyst.

These carboalkyl derivatives may be reduced with LiAlH$_4$ to the corresponding alkyl derivatives before debenzylation thereof.

Starting from the compound (IV) the products of formula (I) are prepared where
R$_3$=carboamido radical by reaction with the appropriate isocyanate and then by debenzylation by treatment with hydrogen on a Pd/C catalyst.

We report hereinafter some illustrative examples which have the purpose of better illustrating the process of the present invention without however in any manner limiting the same.

EXAMPLE 1

Process for the preparation of 1(5-amino-3-hydroxymethyl)phenyl-2-terbutyl amino-ethanol (VAL 5000)

—5-nitro-3-carbomethoxy-αbromoacetophenone

5'-nitroisophthaloyl chloride monomethyl ester (g24,2=0.099 mole) dissolved in ethyl ether was added at $-10°$ C. to an ethanol solution of diazomethane (10 g). After 1 h the precipitate was filtered and suspended in acetic acid (180 ml).

To the suspension enough aqueous 40% HBr was added to ensure complete evolution of nitrogen; water was added and the precipitate was filtered after 12 hours to give 5 nitro-3-carbomethoxy-α-bromoacetophenone (21 g). Yield 70.2% m.p. 69°–70° C.

|  | C | H | N |
|---|---|---|---|
| Analysis - Calculated for C$_{10}$H$_8$BrNO$_5$ | 39.76% | 2.65% | 4.63% |
| Found | 39.13% | 2.62% | 4.59% |

—1-epoxyethyl-5-nitro-3-carbomethoxy benzene

To a stirred solution of the 5 nitro-3-carbomethoxy-α-bromoacetophenone (17.2 g=0.057 mole) in anhydrous methanol (800 ml), NaBH$_4$ 90% (2.90 g=0.078 mole) was added. After being stirred at 10° for 12 hours the solvent was partially evaporated and the solution made acid with 2NH$_2$SO$_4$. The mixture was diluted with ice-water and extracted with ethyl ether. The organic phase was stirred with a solution of KOH (1 g) in H$_2$O (20 ml). The ethereal phase was evaporated to give 1-epoxyethyl-5-nitro-3-carbomethoxy benzene. 12.5 g. Yield 98.2% m.p. 59°–60° C.

|  | C | H | N |
|---|---|---|---|
| Analysis - Calcul. for C$_{10}$H$_9$NO$_5$ | 53.83% | 4.03% | 6.27% |
| Found | 53.02% | 4.00% | 6.21% |

Alternatively to the epoxy-compound the following bromohydrin could be prepared.

—1-(5-nitro-3-carbomethoxy)-phenyl-2 bromo-ethanol

To a stirred solution of the 5-nitro-3-carbomethoxy α-bromoacetophenone —16 g (0.53 mole) in methanol (750 ml)—NaBH$_4$ 99% (3 g=0.071 mole was added. After being stirred at 10° for 12 hours, the solvent was partially evaporated and the solution made acid with 2N H$_2$SO$_4$. The mixture was diluted with ice-water and extracted with ethyl ether. The organic layer was stirred with a solution of KOH (1 g) in H$_2$O (20 ml). The ethereal phase was evaporated to give 1-(5-nitro-3-carbomethoxy) phenyl-2-bromo-ethanol. 13.69 g. Yield 85% m.p. 75°-76° C.

|  | C | H | N % |
|---|---|---|---|
| Analysis - Calcul. for C$_{10}$H$_{10}$BrNO$_5$ | 39.50% | 3.28% | 4.60% |
| Found | 39.42% | 3.20% | 4.53% |

—1-(5-nitro-3-carbomethoxy)phenyl-2-t-butyl-amino-ethanol.

A mixture of 1-epoxyethyl-3-carbomethoxy-5-nitrobenzene (12 g=0.054 mole) and ter-butylamine (14 ml) in 180 ml of methanol was refluxed for 5 hours. After evaporation of the solvent the residue was crystallised from EtOA to give 1-(5-nitro-3-carbomethoxy)phenyl-2-t-butyl-amino-ethanol (10.5 g). Yield 65.7% m.p. 86°-87° C.

|  | C | H | N |
|---|---|---|---|
| Analysis - Calculated for C$_{14}$H$_{20}$N$_2$O$_5$ | 56.78% | 6.75% | 9.45% |
| Found | 55.92% | 6.64% | 9.30% |

The same compound could be prepared starting from 1-(5-nitro-3-carbomethoxy)phenyl-2bromo-ethanol.

A mixture of 1-(5-nitro-3-carbomethoxy)phenyl-2-bromoethanol (12,5 g=0.041 mole) and ter-butylamine (11 ml) in 160 ml of methoanol was refluxed for 5hours. After evaporation of the solvent the residue was treated with NaOH (10%) and extracted with ethyl ether.

The etheral phase was evaporated and the residue crystallised from EtOAc to give 1-(5-nitro-3-carbomethoxy)phenyl-2-t-butylamino-ethanol (6.4 g). Yield 53%. m.p. 86°-87° C.

—1-(5-amino-3-carbometoxy)-phenyl-2-t-butylamino-ethanol

The compound 1-(5-nitro-3-carbomethoxy)phenyl-2-t-butylamino ethanol prepared either from the 1-epoxyethyl-5-nitro-3-carbomethoxy benzene or from 1-(5-nitro-3-carboxmethoxy)phenyl-2-bromo ethanol (11.84 g=0.04 mole) dissolved in ethanol, was shaken under hydrogen in the presence of 10% palladium on carbon (4 g). When the reducton was complete, the catalyst was filtered off and the solution was evaporated to yeld the 1-(5-amino-3-carbomethoxy)-phenyl-2-t-butylamino-ethanol, 10.24 g Yield 96.24% -m.p. 79°-80° C.

|  | C | H | N % |
|---|---|---|---|
| Analysis - Calculated for C$_{14}$H$_{22}$N$_2$O$_3$ | 63.13% | 8.33% | 10.52% |
| Found | 62.9% | 8.04% | 10.40% |

—1-(5-amino-3hydroxymethyl)phenyl-2-terbutyl amino-ethanol (VAL 5000)

A solution of 1-(5-amino3-carbomethoxy)-phenyl-2-terbutylamino ethanol (8 g=0.03 mole) in 140 ml of the THF was added dropwise and under stirring to a boil suspension of LiAlH$_4$ (2.8 g=0.074 mole) in 140 ml of THF, and refluxed for 3 hours. Then 13 ml of water were added. The mixture was filtered and the filtrate was evaporated to give the 1-(5-amino-3 hydroxymethyl)phenyl-2-terbutyl amino-ethanol.

The product was crystallized from EtOAc to give 5.5 g. Yield 77% m.p. 140°-141° C.

|  | C | H | N % |
|---|---|---|---|
| Analysis - Calculated for C$_{13}$H$_{22}$N$_2$O$_2$ | 65.56% | 9.24% | 11.76% |
| Found | 65.69% | 9.41% | 11.66% |

EXAMPLE 2

Process for the preparation of 1-(5-amino-3-hydroxymethyl)phenyl-2-cyclo hexyl amino-ethanol (VAL 5500)

—1-(5-nitro-3-carbomethoxy)phenyl-2-cyclohexylamino-ethanol

A mixture of 1-epoxyethyl-5-nitro-3-carbomethoxybenzene (12 g=0.054 mole) prepared as described in Example 1, and cyclohexylamine (16.9 ml) in 230 ml of methanol was refluxed for 5 hours. The solution was partially evaporated and cooled at 0° for 12 hours. The precipitate was filtered and crystallized from methanol to give 1-(5-nitro-3-carbomethoxy)-phenyl-2-cyclohexylamino-ethanol 8.35 g. Yield 48% m.p. 135°-136° C.

|  | C | H | N |
|---|---|---|---|
| Analysis - Calculated for C$_{16}$H$_{22}$N$_2$O$_5$ | 59.65% | 6.83% | 8.69% |
| Found | 59.58% | 6.70% | 8.59% |

—1-(5-amino-3-carbomethoxy)-phenyl-2-cyclohexylamino-ethanol

Following the procedure of Example 1, the 1-(5-nitro-3-carbomethoxy)phenyl-2-cyclohexylamino ethanol (6.44 g=0.002 mole) was reduced with hydrogen and Pd/C to the 1-(5-amino-3-carbomethoxy)-phenyl-2-cyclohexylamino-ethanol 5 g. Yield 85.5% m.p. 118°-119° C.

|  | C | H | N |
|---|---|---|---|
| Analysis - Calculated for C$_{16}$H$_{24}$N$_2$O$_3$ | 65.77% | 8.21% | 9.58% |
| Found | 66.50% | 8.38% | 9.73% |

—1-(5-amino-3-hydroxymethyl)phenyl-2-cyclohexylamino ethanol (VAL 5500)

Following the procedure of Example 1, the 1-(5-amino-3-carbomethoxy)-phenyl-2-cyclohexylaminoethanol(4,5 g=0.015 mole) was reduced with LiAlH$_4$ to 1-(5-amino-3-hydroxymethyl)-phenyl-2-cyclohexylamino ethanol 2.77 g. Yield 70%

|  | C | H | N |
|---|---|---|---|
| Analysis - Calculated for C$_{15}$H$_{24}$N$_2$O$_2$ | 68.20% | 9.08% | 10.60% |
| Found | 68.30% | 9.33% | 10.82% |

EXAMPLE 3

Process for the preparation of 1-(5-amino-3hydroxymethyl)phenyl-2-(1-p.methoxyphenyl-2-propylamino)ethanol dihydrochloride (VAL 5000/PM)

—1-(5-nitro-3-carbomethoxy)phenyl-2-(1-p-methoxyphenyl-2-propylamino)-ethanol hydrochloride A mixture of 1-epoxyethyl-5-nitro-3-carbomethoxy benzene, prepared according to Example 1, (11 g=0.049 mole) and 1-p-methoxyphenyl-2-propylamine (g 20=0.12 mole) in 300 ml of methanol was refluxed for 5 hours. The solution was evaporated and the excess of 1-p-methoxyphenyl-2-propylamine eliminated by steam distillation. The residue was extracted with EtOAc. The organic layer was evaporated. The residue was dissolved in anhydrous ethyl ether and hydrogen chloride was added to obtain the 1-(5-nitro-3-carbomethoxy)phenyl-2-(1-p-methoxyphenyl-2-propylamino) ethanol hydrochloride g 6.2. Yield 30%. m.p. 186°-187° C.

|  | C | H | N | % |
|---|---|---|---|---|
| Analysis - Calculated for C$_{20}$H$_{25}$ClN$_2$O$_6$ | 56.56% | 5.89% | 6.59% |  |
| Found | 56.37% | 5.87% | 6.48% |  |

—1-(5-amino-3-carbomethoxy)phenyl-2-(1-p-methoxyphenyl-2-propylamino) ethanol dihydrochloride Following the procedure of Example 1 the 1-(5-nitro-3 carbomethoxy)phenyl-2-(1-p-methoxyphenyl-2-propylamino)-ethanol hydrochloride (6 g=0.014 mole) was reduced with hydrogen and Pd/C to 1-(5-amino-3-carbomethoxy)phenyl-2-(1-p-methoxy phenyl-2-propylamino)ethanol hydrochloride. This oily aminoethanol compound was treated with hydrogen chloryde to give the corresponding dihydrochloryde. (5.30 g). Yield 88%. m.p. 240°-242° C. dec.

|  | C | H | N |
|---|---|---|---|
| Analysis - Calculated for C$_{20}$H$_{28}$Cl$_2$N$_2$O$_4$ | 55.70% | 6.49% | 6.49% |
| Found | 55.61 | 6.32 | 6.41 |

—1-(5-amino-3hydroxymethyl)phenyl-2-(1 p-methoxyphenyl-2-propylamino) ethanol dihydrochloride.

(VAL 5000/PM)

Following the procedure of Example 1 the 1-(5-amino-3carbomethoxy)phenyl-2-(1-p-methoxy phenyl-2-propylamino)-ethanol dihydrochloride.

(4.8 g=0.011 mole) was reduced with LiAlH$_4$ to 1-(5 amino-3hydroxymethyl)phenyl 2-(1 p-methoxy phenyl-2-propylamino)ethanol dihydrochloride. 3.19 g. Yield 72%. m.p. 260°-262° C. dec.

|  | C | H | N | % |
|---|---|---|---|---|
| Analysis - Calculated for C$_{19}$H$_{28}$Cl$_2$N$_2$O$_3$ | 56.60% | 6.94% | 6.94% |  |
| Found | 56.41% | 7.00% | 6.81% |  |

EXAMPLE 4

Process for the preparation 1-(5-acetamido-3 hydroxymethyl)-phenyl-2-ter butyl aminoethanol hydrochloride (VAL 5100).

To a solution of 1-(5-amino-3 hydroxy methyl)-phenyl-2-terbutylamino-ethanol prepared according to Example 1 (3 g=0.013 mole) in 120 ml of THF was added acetyl chloride (0.85 ml). The precipitate was filtered and triturated with ethyl ether to yield 1-(5acetamido-3 hydroxymethyl)phenyl-2-ter butylamine ethanol hydrochloride (2.6 g). Yield 63.2%. m.p. 208°-209° C.

|  | C | H | N |
|---|---|---|---|
| Analysis - Calculated for C$_{15}$H$_{25}$ClN$_2$O$_3$: | 56.89% | 7.89% | 8.84% |
| Found | 56.75% | 7.70% | 8.66% |

EXAMPLE 5

Process for the preparation of 1-(5-ethylamino-3-hydroxymethyl)phenyl-2-t.butylamine ethanol (VAL 5600)

—1(5-acetamido-3carbomethoxy)-phenyl-2-t-butylamino ethanol hydrochloride

The 1-(5 amino-3-carbomethoxy)phenyl-2-t-butylamino-ethanol (5 g=0.018 mole) prepared according to Example 3 was acetylated with acetyl chloride to give 1-(5-acetamido-3-carbomethoxy) phenyl-2-t-butylamino ethanol hydrochloride according to the procedure of Example 4. The title compound was obtained in an amount of 6 g, with a yield of 96.7%.

The free base was crystallized from EtOAc to give 4.7 g m.p. 114°-115° C.

|  | C | H | N | % |
|---|---|---|---|---|
| Analysis - Calculated for C$_{16}$H$_{24}$N$_2$O$_4$ | 62.36% | 7.79% | 9.09% |  |
| Found | 62.43% | 7.68% | 8.96% |  |

—1-(5-ethylamino-3-hydroxy methyl) phenyl-2-ter butylamino-ethanol dihydro chloride monohydrate (VAL 5600)

The 1-(5 acetamido-3 carbomethoxy)phenyl-2-ter butylamino-ethanol (4.3 g=0.013 mole) was reduced with LiAlH$_4$ (2.7 g=0.071 mole) following the procedure described in Example 1 to give 1-(5-ethylamino-3 hydroxy methyl)phenyl-2-ter butylamino-ethanol 2.8 g. Yield 74%.

The product dissolved in ethyl ether and treated with hydrogen chloride gave the dihydrochloride which was recrystallized from 2 propanol
m.p. 190°–192° C. dec.

|  | C | H | N | % |
|---|---|---|---|---|
| Analysis - Calculated for $C_{15}H_{28}Cl_2N_2O_2H_2O$ | 50.44% | 7.84% | 7.84% | |
| Found | 50.69% | 7.31% | 7.75% | |

EXAMPLE 6

Process for the preparation of 1-(5-ethylamino-3-hydroxy methyl)phenyl-2-ter-butylaminoethanol dihydrochloride (VAL 5600)

The 1-(5-acetamido-3-hydroxymethyl)phenyl-2-ter butylamino-ethanol (1,2 g=0.004 mole) prepared according to Example 4 was reduced with LiAlH$_4$ to butylamino-ethanol (0.76 g). Yield 71%. The product dissolved in ethyl ether and treated with hydrogen chloride gave the dihydrochloride compound, m.p. 190°–192° dec.

|  | C | H | N |
|---|---|---|---|
| Analysis - Calculated for $C_{15}H_{18}Cl_2N_2O_2$ | 53.13% | 8.26% | 8.26% |
| Found | 52.00% | 8.12% | 8.17% |

EXAMPLE 7

Process for the preparation of 1-(5-acetamido-3-hydroxy-phenyl-2 t.butyl amino-ethanol hydrochloride (VAL 6100).

—5-nitro-3-hydroxy methyl benzoate

The compound 5-nitro-3-hydroxy benzoic and (115 g=0.63 mole) was dissolved in methanol saturated with hydrogen chloride (1750 ml) and refluxed over 7 hours under hydrogen chloride. The solution was partially evaporated and the filtered precipitate was crystallized from water to give 5-nitro-3-hydroxy methyl benzoate 77.22 g. Yield 62.5%
m.p. 155°–156° C.

|  | C | H | N |
|---|---|---|---|
| Analysis - Calculated for $C_8H_7NO_5$ | 48.75% | 3.55% | 7.10% |
| Found | 50.10% | 4.22% | 7.89% |

—5-nitro-3-benzyloxy benzoic acid

A mixture of 5nitro-3-hydroxy-methyl benzoate (50.4 g=0.26 mole), benzyl chloride (32.24 ml), K$_2$CO$_3$ (43.9 g) NaI (3.84 g) and 256 ml of ethanol 95% was stirred and refluxed for 30 hours. The mixture was cooled and diluted with water, acidified and the precipitate filtered and crystallized from 2-propanol to give 5-nitro-3-benzyloxy benzoic acid 96.5 g. Yield 97.9%. m.p. 157°–158° C.

|  | C | H | N |
|---|---|---|---|
| Analysis - Calculated for $C_{14}H_{11}NO_5$ | 61.55% | 4.03% | 5.12% |
| Found | 61.00% | 3.97% | 4.88% |

—5-nitro-3-benzyloxy-benzoyl chloride

A mixture of 5 nitro-3 benzyloxy benzoic acid 40 g (0.146 mole) and PCl$_5$ (30.6 g) was heated at 100°–110° C. until hydrogen chloride evolution ceases. The POCl$_3$ was distilled in vacuo and the residue was crystallized from n-hexane to give 5-nitro-3-benzyloxy-benzoyl chloride 40.89 g. Yield 95.8% m.p. 84°–85° C.

|  | C | H | N |
|---|---|---|---|
| Analysis - Calculated for $C_{14}H_{10}ClNO_4$ | 57.65% | 3.43% | 4.80% |
| Found | 56.92% | 3.01% | 4.64% |

—5-nitro-3-benyloxy-α-bromoacetophenone 5-nitro-3-benyloxy benzoylchloride (32 g=0.11 mole) dissolved in ethyl ether was added at −10° to an ethereal solution of diazomethane (12 g). After 1 hour the precipitate was filtered and suspended in acetic acid (200 ml).

To the suspension enough aqueous 40% HBr was added to ensure complete evolution of nitrogen.

Water was added and the precipitate was filtered after 12 hours to give: 5-nitro-3-benzyloxy-α-bromoacetophenone 28 g. Yield 72.7% m.p. 83°–84° C.

|  | C | H | N | % |
|---|---|---|---|---|
| Analysis - Calculated for $C_{15}H_{12}BrNO_4$ | 51.46% | 3.43% | 4.00% | |
| Found | 51.60% | 3.53% | 4.12% | |

—1-epoxyethyl-5-nitro-3-benzyloxy benzene

To a stirred solution of the 5-nitro-3-benzyloxy-α-bromoacetophenone (26 g=0.074 mole) in anhydrous methanol (1500 ml), NaBH$_4$ 90% (3.82 g=0.101 mole) was added. After being stirred at 10° for 12 hours, the solvent was partially evaporated and the solution made acid with 2NH$_2$SO$_4$. The mixture was diluted with ice-water and extracted with ethyl ether. The organic layer was stirred with a solution of KOH. (1," g) in H$_2$O(26 ml)

The ethereal phase was evaporated to give 1-epoxyethyl-5-nitro-3-benzyloxy benzene g 15.6 g Yield 78%. m.p. 54°–55° C.

|  | C | H | N |
|---|---|---|---|
| Analysis - Calculated for $C_{15}H_{13}NO_4$ | 66.43% | 4.79% | 5.16% |
| Found | 66.70% | 4.72% | 5.00% |

—1-(5-nitro-3-benzyloxy)-phenyl-2-bromo-ethanol

To a stirred solution of the 5 nitro-3-benzyloxy-α-bromoacetophenone (20 g=0.057 mole) in methanol (900 ml), NaBH$_4$ 99% (3.11 g=0.082 mole) was added. After being stirred at 10° for 12 hours, the solvent was partially evaporated and the solution made acid with 2N$_2$SO$_4$. The mixture was diluted with ice water and extracted with ethyl ether. The organic layer was stirred with a solution of KOH. (1 g in H₂O (20 ml).The ethereal phase was evaporated to give 1-(5-nitro-3-benzyloxy)phenyl-2 bromoethanol 13.64 g. Yield 68% m.p. 72°-θ° C.

| | C | H | N |
|---|---|---|---|
| Analysis - Calculated for C₁₅H₁₄BrNO₄ | 51.12% | 3.97% | 3.97% |
| Found | 51.39% | 3.88% | 4.02% |

—1-(5-nitro-3-benzyloxy)phenyl-2-t-butyl amino ethanol hydrochloride

A mixture of 1-oxyethyl-5-nitro-3-benzyloxy-benzene (11.4 g=0.042 mole) and ter-butylamine (11 ml) in 200 ml of methanol was refluxed for 24 hours. After evaporation of the solvent the residue was dissolved in ethyl ether and treated with hydrogen chloride to give 1-(5-nitro-3-benzyloxy)phenyl-2 t-butyl amino ethanol hydrochloride g 13.8. Yield 86.3% m.p. 183°-184° C.

| | C | H | N |
|---|---|---|---|
| Analysis - Calculated for C₁₉H₂₅ClN₂O₄ | 59.94% | 6.57% | 7.36% |
| Found | 60.15% | 6.63% | 7.42% |

Alternatively the same compound could be prepared as follows:

A mixture of 1-(5-nitro-3 benzyloxy)-phenyl-2 bromo ethanol (12 g=0.034 mole) and ter-butylamine (9 ml) in 200 ml of methanol was refluxed for 24 hours. After evaporation of the solvent the residue was treated with NaOH (10% and extracted with ethyl ether. The ethereal phase was treated with hydrogen chloride to give (1-(5-nitro-3-benzyloxy)phenyl-2 t-butylamino ethanol hydrochloride 9.7 g. Yield 75%.
m.p. 183°-184° C.

—1-(5-amino-3-benzyloxy)phenyl-2-t-butylamino-ethanol hydrochloride

The 1-(5-nitro-3-benzyloxy)phenyl-2 t.butyamino ethanol HCl (20 g=0.052 mole) dissolved in 1 l of methenol, was shaken under hydrogen in the presence of PtO₂ (632 mg). When the reduction was complete, the catalyst was filtered off and the solvent was evaporated to yield 1-(5-amino-3-benzyloxy)phenyl-2-t-butylamino-ethanol hydrochloride 16.2 g. Yield 89%. m.p. 120°-121° C.

| | C | H | N |
|---|---|---|---|
| Analysis - Calculated for C₁₉H₂₇ClN₂O₂ | 65.07% | 7.70% | 7.99% |
| Found | 66.10% | 7.81% | 8.05% |

—1-(5 acetamido-3-benzyloxy) phenyl-2 t-butylamino ethanol hydrochloride

The 1-(5-amino-3-benzyloxy)phenyl-2 t-butylamino ethanol hydrochloride 15 g (0.042 mole) was dissolved in HCl^dil (120 ml). The pH was raised to 4 by Na₂CO₃ and acetic anhydride (42 ml) was added dropwise. After 3 hours the precipitate was filtered to give 1-(5-acetamido-3-benzyloxy)phenyl-2 t-butylamino ethanol hydrochloride 14 g. Yield 84.9%. m.p. 195°-196° C.

| | C | H | N |
|---|---|---|---|
| Analysis - Calculated for C₂₁H₂₉ClN₂O₃ | 64.22% | 7.38% | 7.13% |
| Found | 63.98% | 7.15% | 7.03% |

—1-(5-acetamido-3-hydroxy)-phenyl-2 t butylamino ethanol hydrochloride. (VAL 6100)

The 1-(5-acetamido-3 benzyloxy)phenyl-2 t-butylamino ethanol hydrochloride (10 g=0.025 mole) dissolved in 400 ml of ethanol was shaken under hydrogen in the presence of 10% palladium on carbon (2.699 g). When the reduction was complete the catalyst was filtered off and the solvent was evaporated to yield 1-(5-acetamido-3 hydroxy)phenyl-2 t butylamino ethanol hydrochloride 6.42 g. Yield 85%. m.p. 114°-115° C.

| | C | H | N |
|---|---|---|---|
| Analysis - Calculated for C₁₄H₂₃ClN₂O₃ | 55.55% | 7.59% | 9.25% |
| Found | 55.61% | 7.73% | 9.32% |

EXAMPLE 8

Process for the preparation of 1-(5-acetamido-3-hydroxy)phenyl-2-cyclohexyl amino ethanol hydrochloride (VAL 6500/6100)

—1-(5-nitro-3-benzyloxy)phenyl-2 cyclohexylamino-ethanol hydrochloride 1-epoxyethyl-5-nitro-3-benzyloxy benzene (12 g=0.044 mole) prepared according to Example 7 and cyclohexylamine (13.4 ml), yielded always according to Example 7 1-(5-nitro-3-benzyloxy)phenyl-2 cyclohexylamino-ethanol hydrochloride 15.2 g. Yield 85%. m.p. 189°-190 C.

| | C | H | N |
|---|---|---|---|
| Analysis - Calculated for C₂₁H₂₇ClN₂O₄ | 62.01% | 6.64% | 6.88% |
| Found | 62.07% | 6.82% | 6.93% |

—1-(5-nitro-3-benzyloxy)phenyl-2-cyclohexylamino-ethanol hydrochloride

The 1-(5-nitro-3-benzyloxy)phenyl-2-cyclohexylamino-ethanol hydrochloride (12 g=0.029 mole) was reduced with hydrogen and PtO₂ according to example 7 to the 1-(5-amino-3-benzyloxy)phenyl-2 cyclohexylamino-ethanol hydrochloride 10 g. Yield 92%. m.p. 166°-167° C.

| | C | H | N |
|---|---|---|---|
| Analysis - Calculated C₂₁H₂₉ClN₂O₂ | 66.95% | 7.89% | 7.43% |
| Found | 66.72% | 7.70% | 7.31% |

—1-(5-acetamido-3-benzyloxy)phenyl 2 cyclohexylamino ethanolhydrochloride

The 1-(5-amino-3-benzyloxy)phenyl-2 cyclohexylamino ethanol hydrochloride (8 g=0.02 mole) was acetylated according to example 7 to 1-(5 acetamido-3- benzyloxy)phenyl 2 cyclohexylamino ethanol hydrochloride 7.19 g. Yield 86%. m.p. 216°–218° C.

|  | C | H | N |
|---|---|---|---|
| Analysis - Calculated for $C_{23}H_{31}ClN_2O_3$ | 65.96% | 7.40% | 6.69% |
| Found | 66.08% | 7.55% | 6.72% |

—1-(5 acetamido-3-hydroxy)phenyl-2-cyclohexylamino ethanol hydrochloride (VAL 6500/6100)

The 1-(5-acetamido-3-benzyloxy)phenyl-2 cyclohexylamino ethanol hydrochloride (5 g=0.012 mole) was debenzylated according to Example 7 to give 1-(5 acetamido-3-hydroxy)phenyl-2 cyclohexylamino ethanol hydrochloride 3.45 g. Yield 88%. m.p. 243°–244° dec

|  | C | H | N |
|---|---|---|---|
| Analysis - Calculated for $C_{16}H_{25}ClN_2O_3$ | 58.46% | 7.60% | 8.52% |
| Found | 58.36% | 7.72% | 8.20% |

EXAMPLE 9

Process for the preparation of 1-(5-ureido-3-hydroxy)phenyl-2 t.butylamino ethanol (VAL 6300)

—1-(5 ureido-3-benzyloxy)-phenyl-2 t-butylamino ethanol

The 1-(5-amino-3-benzyloxy)phenyl-2-t-butylamino ethanol hydrochloride (2 g=0.0057 mole) prepared according to example 7 was dissolved in a solution of acetic acid (10 ml) and $H_2O$ (60 ml). To this solution was added dropwise a solution of NaCNO (370 mg) in $H_2O$ (30 ml). After 30 minutes the pH of the solution was raised with ammonia and the solution was extracted with EtOAc. The organic phase was evaporated to give 1-(5-ureido-3-benzyloxy)phenyl-2 t-butylamino ethanol 1.2 g. Yield 58.9% m.p. 156°–157° C.

|  | C | H | N |
|---|---|---|---|
| Analysis - Calculated for $C_{20}H_{27}H_3O_3$ | 67.24% | 7.56% | 11.76% |
| Found | 67.01% | 7.38% | 11.62% |

—1-(5-ureido-3-hydroxy)-phenyl-2 t-butyl amino ethanol (VAL 6300)

The compound 1-(5-ureido-3-benzyloxy)-phenyl-2 t-butylamino ethanol (1 g=0.0028 mole) dissolved in 50 ml of ethanol, was shaken under hydrogen in the presence of 10% palladium on carbon (260 mg). When the reduction was complete, the catalyst was filtered off and the solvent was evaporated to yield 1-(5-ureido-3-hydroxy)phenyl-2 t-butyl amino ethanol 695 mg (92%). m.p. 105°–106° C.

|  | C | H | N |
|---|---|---|---|
| Analysis - Calculated for $C_{13}H_{21}N_3O_3$ | 58.44% | 7.86% | 15.72% |
| Found | 58.29% | 7.81% | 15.62% |

EXAMPLE 10

Process for the preparation of 1-(5-ureido-3-hydroxy)phenyl-2-cyclohexylamino ethanol (VAL 6500)

—1-(5-ureido-3-benzyloxy)phenyl-2-cyclohexylamino ethanol

Following the procedure of example 9 the 1-(5-amino-3-benzyloxy)phenyl-2 -cyclohexylamino ethanol hydrochloride (3 g=0.0079 mole) prepared according to the procedure described in Example 7 for the corresponding t-butylamino compound, was reacted with NaCNO according to example 9 to give the 1-(5 ureido-3-benzyloxy) phenyl-2 cyclohexylamino ethanol 1.86 g. Yield 61%. m.p. 154°–155° C.

|  | C | H | N |
|---|---|---|---|
| Analysis - Calculated for $C_{22}H_{29}N_3O_3$ | 68.94% | 7.56% | 10.96% |
| Found | 68.81% | 7.42% | 11.02% |

—1-(5-ureido-3-hydroxy) phenyl-2 cyclohexylamino ethanol (VAL 6500/6300)

The 1-(5 ureido-3 benzyloxy)-phenyl-2-cyclohexyalmino ethanol (1.5 g=0.003 mole) was debenzylated to 1-(5-ureido-3-hydroxy) phenyl-2 cyclohexylamino ethanol (g 1.069; Yield 90%,) exactly as described in example 9 for the corresponding tibutylamino derivative. m.p. 127°–128° C.

|  | C | H | N |
|---|---|---|---|
| Analysis - Calculated for $C_{15}H_{23}N_3O_3$ | 61.45% | 7.84% | 14.32% |
| Found | 61.10% | 7.67% | 14.15% |

All the remaining compounds of formula I have been prepared through the process described in detail in the preceeding examples.

As initially stated, the new compounds of the present invention are endowed with strongly selective bronchodilating activity. In order to demonstrate the advantageous properties of the new compounds, we report hereinafter, for some significant term of the serie the date illustrating the activity on the bronchi, cardiac and uterus smooth muscles, in comparison with Orciprenaline, a compound of the formula

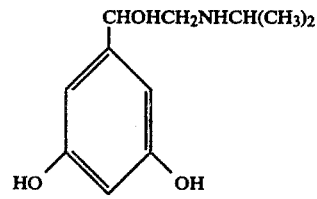

which is the best among the 3,5 phenyl-aminoethanols prepared up today. From the reported data it is immediately evident that in the experimental bronchospasm according to Konzett H., Rössler, R., (Arch. f. exp.-Phatol. Pharmakol. 193.71 (1940)) the new compounds need to be administered by parenteral route at higher doses than Orciprenaline (for comparison purposes we may remember that Theophylline is active in this test at 25000 mcg/kg i.v. (J. L. Duhault et al. Arzneim-Forsch 24, 12, 1970 (1974)). The relative potency referred to Orciprenaline is between 1/41–1/200 but they are extremely less active than Orciprenaline on the cardiac muscle: in fact the relative potency referred to Orciprenaline, in the test of stimulating guinea pig isolated atria, is 1/1025 and >1/2500. On the other hand the new compounds of the invention when administered by aerosol (which is the usual route when treating bronchospasm) have an activity comparable with that of Orciprenaline. When, for example, the product VAL 5000/PM is administered by inhalation according to Armitage method, (Armitage, A. K., Boswood, J., Large, B., Brit. J. Pharmacol, 16, 59 (1961)), for preventing the bronchospasm induced by Acetilcholine in conscious giunea pig, we have the following mean values of "time before sign dispnea," expressed in seconds:

VAL 5000/PM=475±60
Orciprenaline=502±67

The new compounds are also valuable uterine relaxant as it appears from Table 1, where the potency referred to Orciprenaline is between ¼ and 1/7, but without any adverse cardiac effect.

The new compounds are very good from an acute toxicity viewpoint.

For example, the new compound VAL 5000/PM has an $LD_{50}=295$ (177–314) mg/kg according to Litchfield and Wilcoxon - J. Pharm. Exp. Th. 95, 99–1949, comparable with the $LD_{50}=380$ (342–422) for Orciprenaline.

The pharmacological effects of the new compounds are inhibited by $\beta$-blockers as Propanolol, so indicating their $\beta_2$ specificity.

The new compounds may be administered by oral, parenteral or aerosol route.

For oral administration they are combined with diluents as lactose and cellulose and prepared as tablets. For parenteral administration they are dissolved preferably in a saline vehicle and put into vials. The aerosols are prepared disperding the compounds into usual vehicles such as isopropyl myristate.

We claim:

1. A compound selected from the group consisting of 1-(5-amino-3-hydroxymethyl)phenyl-2- (1-p.methoxyphenyl-2-propylamino)ethanol and pharmaceutically acceptable acid addition salts thereof.

2. A therapeutic composition useful as a bronchodilator comprising a bronchodilator effective amount of 1-(5-amino-3-hydroxymethyl)phenyl-2-(1-p.methoxyphenyl-2-propylamino)ethanol and a pharmaceutically acceptable carrier.

TABLE 1

| Compounds | Inhibiting Guinea Pig airway constriction (Konzett-Rossleri) (mcg/kg i) | Relative pharmacological potency $\left(\frac{compound}{orciprenaline}\right)$ | Stimulating Guinea Pig isolated Atria (mcg/ml) | Relative pharmacological potency $\left(\frac{compound}{orciprenaline}\right)$ | Reducing tonus and motility of rat uterus (mcg/ml) | Relative pharmacological potency $\left(\frac{compound}{orciprenaline}\right)$ |
|---|---|---|---|---|---|---|
| | + | | + | | + | |
| VAL 5500 | 2000 | 50 | Inactive at 100 | >2500 | 0.25 | 6,2 |
| VAL 5000/PM' | 1640 | 41 | | 41 | 0.16 | 4 |
| VAL 6500/6300 | 8000 | 200 | Inactive at 100 | >2500 | 0.3 | 7,5 |
| Orciprenaline | 40 | 1 | | 0.04 | 0.04 | 1 |

+ Equiactive doses